(12) United States Patent  (10) Patent No.: US 6,514,198 B2
Ishibiki  (45) Date of Patent: Feb. 4, 2003

(54) ENDOSCOPE CAPABLE OF UNDERGOING AT LEAST ONE OF CLEANING, DISINFECTION, AND STERILIZATION AT HIGH TEMPERATURE

(75) Inventor: Kouta Ishibiki, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 14 days.

(21) Appl. No.: 09/908,012

(22) Filed: Jul. 18, 2001

(65) Prior Publication Data

US 2002/0016525 A1 Feb. 7, 2002

(30) Foreign Application Priority Data

Jul. 25, 2000 (JP) .......................................... 2000-224381

(51) Int. Cl.[7] .................................................. A61B 1/00

(52) U.S. Cl. ......................... 600/133; 600/131; 600/139

(58) Field of Search ................................ 600/101, 128, 600/130, 131, 133, 139, 140

(56) References Cited

U.S. PATENT DOCUMENTS 5,871,441 A  *  2/1999  Ishiguro et al. ............. 600/133
6,390,972 B1 *  5/2002  Speier et al. ................. 348/73

FOREIGN PATENT DOCUMENTS

JP          5-337171       12/1993
JP          10-286218      10/1998

* cited by examiner

Primary Examiner—John Mulcahy
(74) Attorney, Agent, or Firm—Scully, Scott, Murphy & Presser (57) ABSTRACT

An endoscope can undergo at least one of cleaning, disinfection, and sterilization at high temperature. The endoscope includes an elongated insertion member and a control section joined to the proximal end of the insertion member. A drop in the temperature of at least part of the outer surface of the insertion member occurring when the endoscope is cooled to predetermined temperature after being processed at high temperature is substantially equal to or larger than a drop in the temperature of at least part of the outer surface of any member other than said part of the outer surface of the insertion member.

27 Claims, 3 Drawing Sheets

ENDOSCOPE CAPABLE OF UNDERGOING AT LEAST ONE OF CLEANING, DISINFECTION, AND STERILIZATION AT HIGH TEMPERATURE

This application claims benefit of Japanese Application No. 2000-224381 filed in Japan on Jul. 25, 2000, the contents of which are incorporated by this reference.

BACKGROUND OF THE INVENTION

1. Field of the Invention

The present invention relates to an endoscope having an elongated insertion member and a control section and capable of undergoing at least one of cleaning, disinfection, and sterilization at high temperature.

2. Description of the Related Art

Today, endoscopes having an elongated insertion member thereof inserted into a body cavity in order to observe a deep region in the body cavity, or if necessary, having a therapeutic instrument used in combination in order to perform a cure or treatment are widely used in the field of medicine. For the medical endoscope, it is essential that a used endoscope should be reliably disinfected or sterilized.

In recent years, autoclaving (high-temperature high-pressure steam sterilization) has become a mainstream method of sterilizing medical equipment. This is because the autoclaving is not labor-intensive and low-cost. Besides, an endoscope can be reused immediately after being autoclaved.

Typical conditions for autoclaving are stipulated in the U.S. standard ANSI/AAMI ST37-1992 recommended by the American National Standards Institute (ANSI) and published from the Association for the Advancement of Medical Instrumentation (AAMI). According to the standard, a pre-vacuum sterilization process should be performed at 132° C. for four min, and a gravity settling sterilization process should be performed at 132° C. for ten min.

The conditions for autoclaving are quite severe for endoscopes. In order to realize an endoscope capable of being autoclaved under the above conditions, measures must be taken. Specifically, the endoscope must withstand high pressure, high temperature, and steam, though an endoscope reusable after being disinfected or sterilized according to any other method need not.

In particular, an insertion member of an endoscope that is a member to be inserted into a patient body is required to exhibit various delicate properties including flexibility and resiliency. The insertion member is more likely to deteriorate when exposed to high pressure, high temperature, or steam than a distal rigid part. Therefore, more sophisticated measures must be taken for the insertion member.

A conventional endoscope capable of being autoclaved is heated to have temperature of 130° C. or more during autoclaving. After completion of the autoclaving, when the temperature of the insertion member thereof returns to room temperature, the endoscope is reused for endoscopic examination.

However, as far as the conventional endoscope capable of being autoclaved is concerned, after autoclaving is completed, a user must wear, for example, clean gloves so as to hold the insertion member with his/her hands for the purpose of checking the temperature of the insertion member.

After autoclaving is completed, a user holds the insertion member firmly with his/her hands so as to check the temperature of the insertion member. At this time, if the temperature of the insertion member is rather high, since the insertion member is soft, a sheathing resin coated over a soft flexible tube that is an integral part of the insertion member may be damaged or deformed.

Otherwise, a control section joined to the proximal end of the insertion member may be touched in order to check the temperature thereof. In this case, even if the temperature of the control section is low, the temperature of the insertion member may be still high.

SUMMARY OF THE INVENTION

Accordingly, an object of the present invention is to provide an endoscope making it possible to reliably and easily check if the temperature of an insertion member thereof has decreased to a level permitting use for examination without the necessity of holding the insertion member after completion of autoclaving.

Briefly, an endoscope in accordance with the present invention can undergo at least one of cleaning, disinfection, and sterilization at high temperature. The endoscope has an elongated insertion member, a control unit joined to the proximal end of the insertion member. A drop in the temperature of at least part of the outer surface of the insertion member occurring when the endoscope is cooled at predetermined temperature after being processed at high temperature is substantially equal to or larger than a drop in the temperature of at least part of the outer surface of any member other than the insertion member. Therefore, by holding at least part of the outer surface of any member other than the insertion member, it can be checked if the temperature of the insertion member has decreased to a level permitting use for examination.

An endoscope in accordance with the present invention. can undergo at least one of cleaning, disinfection, and sterilization at high temperature. The endoscope includes an elongated insertion member, and a control section joined to the proximal end of the insertion member. A drop in the temperature of at least part of the outer surface of the insertion member occurring when the endoscope is cooled at predetermined temperature after being processed at high temperature is substantially equal to or larger than a drop in the temperature of at least part of the outer surface of any member other than the insertion member.

DESCRIPTION OF THE PREFERRED EMBODIMENTS

Referring to the drawings, an embodiment of the present invention will be described below.

Figure 1:
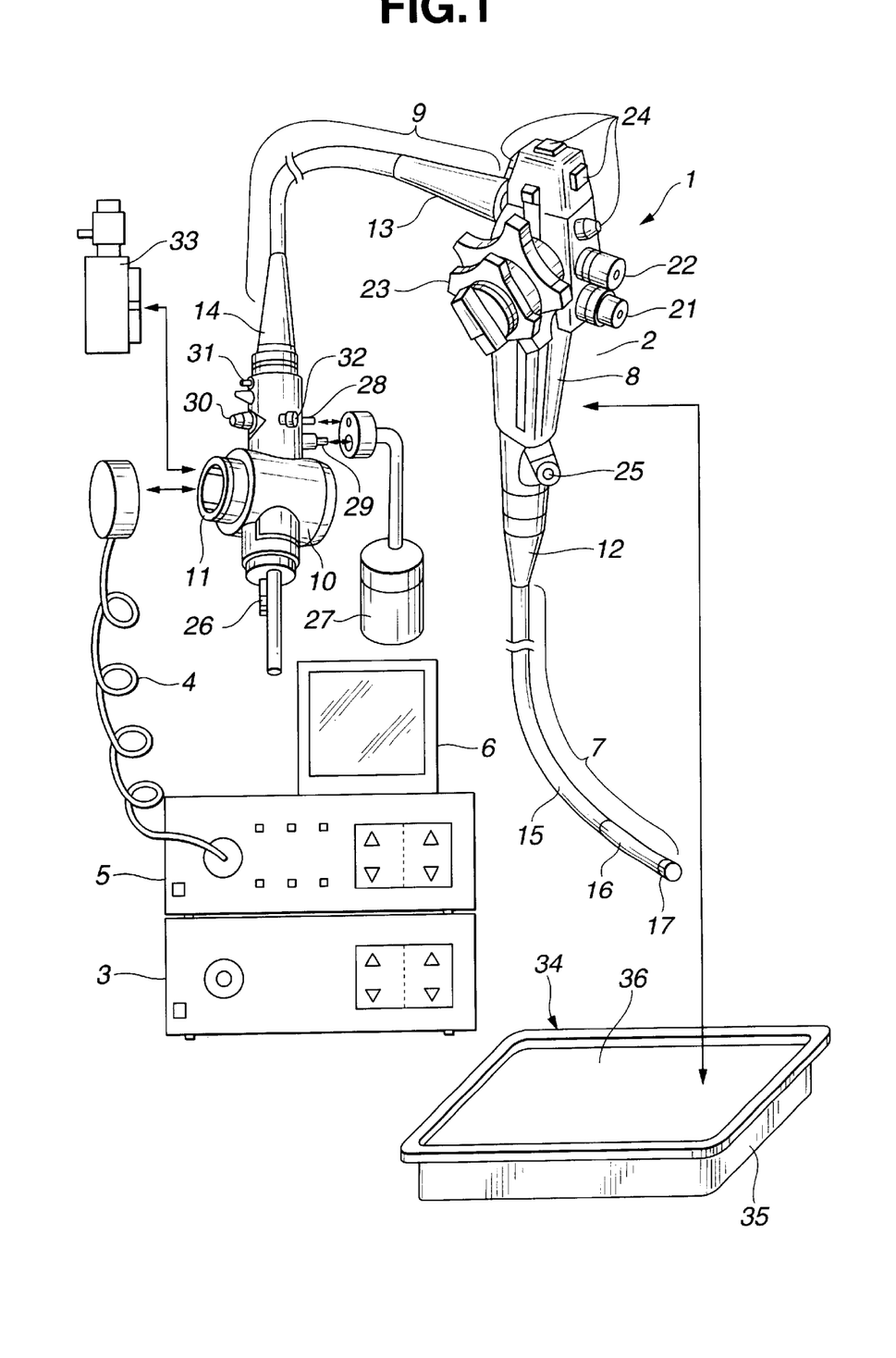
FIG. 1 is an explanatory diagram showing the outline configuration of a system including an endoscope in accordance with the present invention.

As shown in FIG. 1, an endoscope system 1 comprises an endoscope 2, a light source apparatus 3, a video processor 5, and a monitor 6.

The endoscope 2 includes an imaging means (not shown). The light source apparatus 3 is connected to the endoscope 2 so that it can be disconnected freely, and supplies illumination light to a light guide (not shown) and that runs through the endoscope 2. The video processor 5 is connected to the endoscope 2 through a signal cable 4. The video processor 5 controls the imaging means included in the endoscope 2, processes an image signal generated by the imaging means, and outputs a standard video signal. The video signal generated by the video processor 5 is outputted to the monitor 6, whereby an endoscopic image is displayed on the monitor 6.

The endoscope 2 is constituted such that, after used for observation or treatment, the endoscope 2 can be cleaned and sterilized according to a high-temperature high-pressure steam sterilization method (hereinafter, autoclaving).

The endoscope 2 comprises an elongated insertion member 7, a control section 8, and a universal cord 9.

The insertion member 7 is flexible. The control section 8 is joined to the proximal end of the insertion member 7. The universal cord 9 is extended from the lateral part of the control section 8. A connector unit 10 is fixed to an end of the universal cord 9. The connector unit 10 can be freely connected to or disconnected from the light source apparatus 3. An electric connector 11 to or from which the signal cable 4 is freely coupled or uncoupled is formed on the lateral part of the connector unit 10. The signal cable 4 is coupled to the video processor 5.

An insertion member anti-breakage member 12 that includes an elastic member is mounted on a joint between the insertion m ember 7 and control section 8. The insertion member anti-breakage member 12 prevents abrupt bending of the joint. Likewise, a control section anti-breakage member 13 is mounted on a joint between the control section 8 and universal cord 9. A connector unit anti-breakage member 14 is mounted on a joint between the universal cord 9 and connector unit 10.

The insertion member 7 comprises a flexible tube 15, a bending section 16, and a distal part 17. The flexible tube 15 is flexible and soft. The bending section 16 is formed at the distal end of the flexible tube 15. The bending section 16 is bent in predetermined directions by manipulating an angling knob, which will be described later, of the control section 8. An observation optical system and an illumination optical system (not shown) are incorporated in the distal space of the distal part 17.

The control section 8 has an aeration/perfusion button 21, a suction button 22, an angling knob 23, a plurality of remote control switches 24, and a therapeutic instrument insertion port 25. The aeration/perfusion button 21 is used to instruct aeration or perfusion. The suction button 22 is used to instruct suction. The angling knob 23 is used to bend the bending section 16. The remote control switches 24 are used to remotely control the video processor 5. The therapeutic instrument insertion port 25 opens onto a therapeutic instrument channel that runs through the insertion member.

The distal part 17 has a fluid supply port and an aeration/perfusion nozzle (not shown) to jet out a cleaning fluid or gas toward an observation window of the observation optical system when aeration or perfusion is instructed. A suction port (not shown) that is an opening at the distal end of a therapeutic instrument channel running through the insertion member 7 is located in the distal part 17.

The connector unit 10 has a gas supply base 26, a water supply tank pressurization base 28, a fluid supply base 29, a suction base 30, an injection base 31, and a ground base 32.

The gas supply base 26 is connected to a gas source (not shown) incorporated in the light source apparatus 3, so that it can be disconnected freely. The water supply tank pressurization base 28 and fluid supply base 29 are connected to a water supply tank 27 serving as a fluid source so that it can be disconnected freely. The suction base 30 is connected to a suction device (not shown) that sucks a fluid through the suction port in the distal part 17. The injection base 31 is connected to a water supply means (not shown) that supplies water through the fluid supply port in the distal part 17. The ground base 32 is used to feed back high-frequency leakage current to a diathermy device when the leakage current is generated in the endoscope during diathermy.

The electric connector 11 has an air vent hole (not shown) that links the interior of the endoscope 2 and the exterior thereof. Moreover, a pressure regulating valve-inclusive waterproof cap 33 is attached to the electric connector 11 so that it can be freely detached. The waterproof cap 33 has a pressure regulating valve (not shown).

A sterilization case (hereinafter a casing) 34 is used to autoclave the endoscope 2.

The casing 34 comprises a tray 35 in which the endoscope 2 is stowed and a lid member 36. The tray 35 and lid member 36 each have a plurality of pours (not shown). During autoclaving, steam can pass through the pours.

The tray 35 has a restricting portion (not shown) that fits the endoscope 2. The restricting portion is contoured so that the respective components of the endoscope 2 can be settled at respective predetermined positions therein. Moreover, the restricting portion has an insertion member restricting portion (not shown) in which the insertion member 7 with flexibility is stowed.

Typical conditions for high-temperature high-pressure steam sterilization are, as mentioned above, stipulated in the U.S. standard ANSI/AAMI ST37-1992 recommended by the the American National Standards Institute (ANSI) and published from the Association for the Advancement of Medical Instrumentation (AAMI).

The condition of the temperature for high-temperature high-pressure steam sterilization varies depending on the model of a high-temperature high-pressure steam sterilizer or the time required for the sterilization. Generally, the temperature ranges from about 115° C. to about 138° C. Some sterilization devices can be set to about 142° C.

The condition of the time varies depending on the condition of the temperature for sterilization. Generally, the time ranges from about 30 min to about 60 min. Some types of sterilization devices can be set to about 100 min.

The pressure in a sterilization chamber used for the sterilization is generally set to a value larger by 0.2 MPa than the atmospheric pressure.

A typical pre-vacuum type high-temperature high-pressure steam sterilization process includes a pre-vacuum step and a sterilization step. At the pre-vacuum step, a sterilization chamber in which equipment to be sterilized is stowed is decompressed in preparation for sterilization. At the sterilization step that succeeds the pre-vacuum step, high-pressure high-temperature steam is fed into the sterilization chamber for sterilization.

The pre-vacuum step is needed in order to infiltrate steam into every part of the equipment to be sterilized. By decompressing the sterilization chamber, high-pressure high-temperature steam permeates the equipment to be sterilized. The pressure in the sterilization chamber at the pre-vacuum step is set to a value that is smaller by a value ranging from 0.07 MPa to 0.09 MPa than the atmospheric pressure.

In order to dry the equipment to be sterilized that has been sterilized, a dry step at which the sterilization chamber is decompressed again may succeed the sterilization step. At the dry step, the sterilization chamber is decompressed in order to remove steam from the sterilization chamber so as to facilitate drying of the equipment to be sterilized placed in the sterilization chamber. The pressure in the sterilization chamber at the dry step is set to a value that is smaller by a value ranging from 0.07 MPa to 0.09 MPa than the atmospheric pressure.

In order to autoclave the endoscope 2, the pressure regulating valve-inclusive waterproof cap 33 is attached to the electric connector 11. At this time, the pressure regulating valve (not shown), of the waterproof cap 33 is closed. Consequently, the air vent hole of the endoscope 2 is blocked with the waterproof cap 33, and the interior of the endoscope is shut off from the exterior thereof and kept watertight.

When a sterilization method includes the pre-vacuum step, the pressure in the sterilization chamber decreases at the pre-vacuum step. A difference in pressure occurs between the interior and exterior of the endoscope 2. In other words, the external pressure of the endoscope gets lower than the internal pressure thereof. Consequently, the pressure regulating valve opens and the interior of the endoscope 2 communicates with the exterior thereof through the air vent hole. This prevents occurrence of a large difference in pressure between the interior of the endoscope 2 and the sterilization chamber. The endoscope 2 is thus protected from being broken due to a difference in pressure between the interior and the exterior of the endoscope 2.

At the sterilization step, the sterilization chamber is pressurized. A difference in pressure occurs, that is, the external pressure of the endoscope 2 gets higher than the internal pressure thereof. At this time, the pressure regulating valve is closed. Consequently, high-pressure high-temperature steam will not actively permeate the interior of the endoscope 2 through the waterproof cap 33 and air vent hole.

However, high-temperature high-pressure steam permeates the interior of the endoscope through a sheathing of the flexible tube or O rings. The sheathing is made of a high polymer material. The O rings are sealing means included in joints, which join the components of the housing of the endoscope 2, and made of a fluorocarbon rubber or the like. Incidentally, pressure directed from outside to inside is applied to the housing of the endoscope 2. The pressure is the sum of pressure released during decompression at the pre-vacuum step and pressure added at the sterilization step.

When a sterilization method has a decompression step preceded by the sterilization step, the pressure in the sterilization chamber decreases at the decompression step. When a difference in pressure occurs between the interior and exterior of the endoscope 2, that is, the external pressure of the endoscope 2 gets lower than the internal pressure thereof, the pressure regulating valve opens nearly at the same time. Consequently, the interior and exterior of the endoscope 2 communicates with each other through the air vent hole. This prevents occurrence of a large difference in pressure between the interior of the endoscope 2 and the sterilization chamber. Consequently, the endoscope 2 is protected from being broken due to a difference in pressure between the interior and exterior thereof.

When the internal pressure becomes equal to the external pressure, the pressure regulating valve closes. When the sterilization step is completed, the pressure in the sterilization chamber becomes equal to the atmospheric pressure.

As mentioned above, when all the steps of high-temperature high-pressure steam sterilization are completed, pressure directed from outside to inside is applied to the housing of the endoscope 2. The pressure is equivalent to pressure released during decompression at the sterilization step.

When the waterproof cap 33 is detached from the electric connector 11, the interior of the endoscope 2 communicates with the exterior thereof through the air vent hole. Consequently, the internal pressure of the endoscope 2 becomes equal to the atmospheric pressure. The housing of the endoscope 2 is unloaded from the applied pressure.

As mentioned above, the endoscope 2 is cooled at predetermined temperature after being autoclaved. When the temperature of the endoscope 2 returned to room temperature, the endoscope 2 is reused for endoscopic examination.

According to the present embodiment, when the endoscope is cooled at predetermined temperature, a drop in the temperature of at least part of the outer surface of the insertion member 7 is substantially equal to or larger than a drop in the temperature of at least part of the outer surface of any member other than the insertion member 7.

Figure 2:
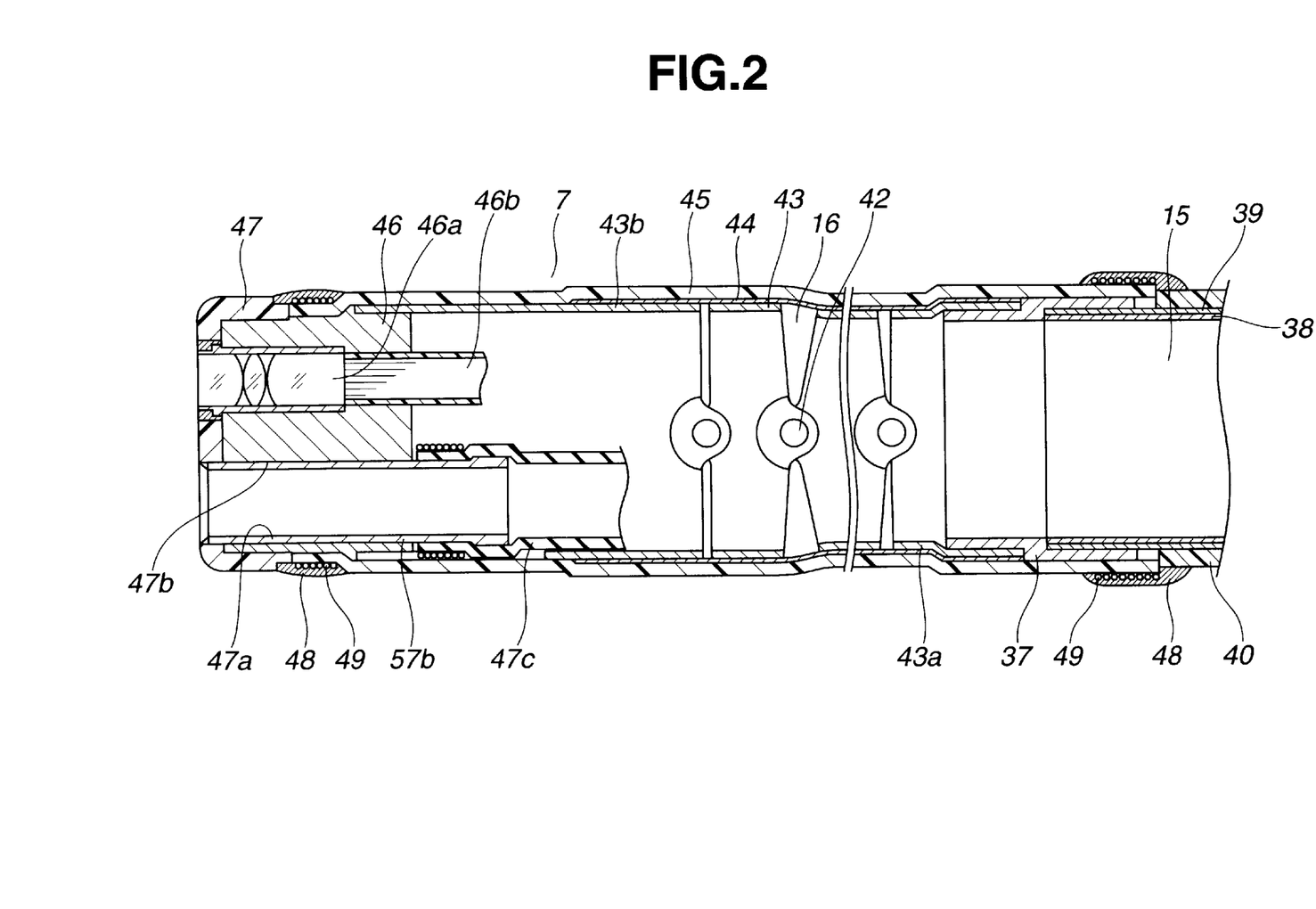
FIG. 2 is a sectional view showing the structure of a distal part of an insertion member of the endoscope.

As shown in FIG. 2, according to the present embodiment, the proximal end of the bending section 16 is integrally fixed to a distal base 37 using a screw (not shown) or the like. The distal base 37 that constitutes the flexible tube 15 is made of a stainless steel or aluminum.

The flexible tube 15 comprises a spiral tube 38, a braid 39, and a sheathing layer 40 that are layered in that order from inside. The spiral tube 38 is made by spirally winding metallic belts. The braid 39 is made by plaiting stainless steal wires or any other metallic wires in the form of a net so that the braid 39 will cover the spiral tube 38 while being in close contact with the outer circumference of the spiral tube 38. The sheathing layer 40 covers the braid 38 while being in close contact with the outer circumference of the braid 38, and is made of an amide elastomer, a styrene resin, a fluorocarbon rubber, or a silicon rubber.

Articulation members 43 made of a metal such as a stainless steal constitute the bending section 16 and are concatenated using rivets 42 so that they can rotate freely. The outer circumference of the plurality of concatenated articulation members 43 is sheathed with a braid 44 that is made by plaiting metallic thin wires. Furthermore, the outer circumference of the braid 44 is sheathed with a sheathing tube 45 that is flexible and made of a resin such as a fluorocarbon rubber.

An articulation member 43a located at the proximal end is engaged with the distal base 37 of the flexible tube 15 and integrally secured using a screw (not shown). A distal articulation member 43b is integrally fixed to a distal body 46 using a screw or the like (not shown). The distal body 46 is made of a metal such as a stainless steel and has an objective optical system (not shown) incorporated therein.

An insulating cover member 47 made of a resin that exhibits excellent chemical resistance and resists high temperature that is higher than the temperature for high-temperature high-pressure steam sterilization is engaged with the outer circumference of the distal body 46. The distal body 46 is made of polyphenylsulfone, polysulfone, polyethersulfone, polyether ether ketone, or the like.

An illumination lens unit 46a is provided in the distal body 46. The illumination lens unit 46a emits illumination light, which is propagated from the light source apparatus 3 through a light guide 46b, to an object.

A metallic channel pipe 47b is passed through a channel pipe hole 47a that penetrates through the distal body 46 and the insulating cover member 47 alike. The distal part of a channel tube 47c is fitted to the outer circumference of the proximal part of the channel pipe 47b.

The distal part of the sheathing tube 45 covers the proximal part of the distal body 46. The distal end surface of the sheathing tube 45 is substantially contacted with the proximal end surface of the insulating cover member 47.

On the other hand, the proximal end of the sheathing tube 45 covers the distal part of the flexible tube 15, and is substantially contacted with the distal end of the sheathing layer 40.

Both the ends of the sheathing tube 45 are tightened by winding a fixing string 49 around the outer circumference of the sheathing tube 45. The sheathing tube 45 is thus fixed to the distal body 46 and distal base 37, which are located inside respective ends of the sheathing tube 45, by winding a string.

An adhesive 48 made of an epoxy resin or the like is applied to the outer surface of the fixing string 49 so that the adhesive 48 will infiltrate into the sheathing tube 45, the fixing string 49, and insulating cover member 47. The fixing string 49 is thus covered. Moreover, the border between the insulating cover member 47.

Figure 3:
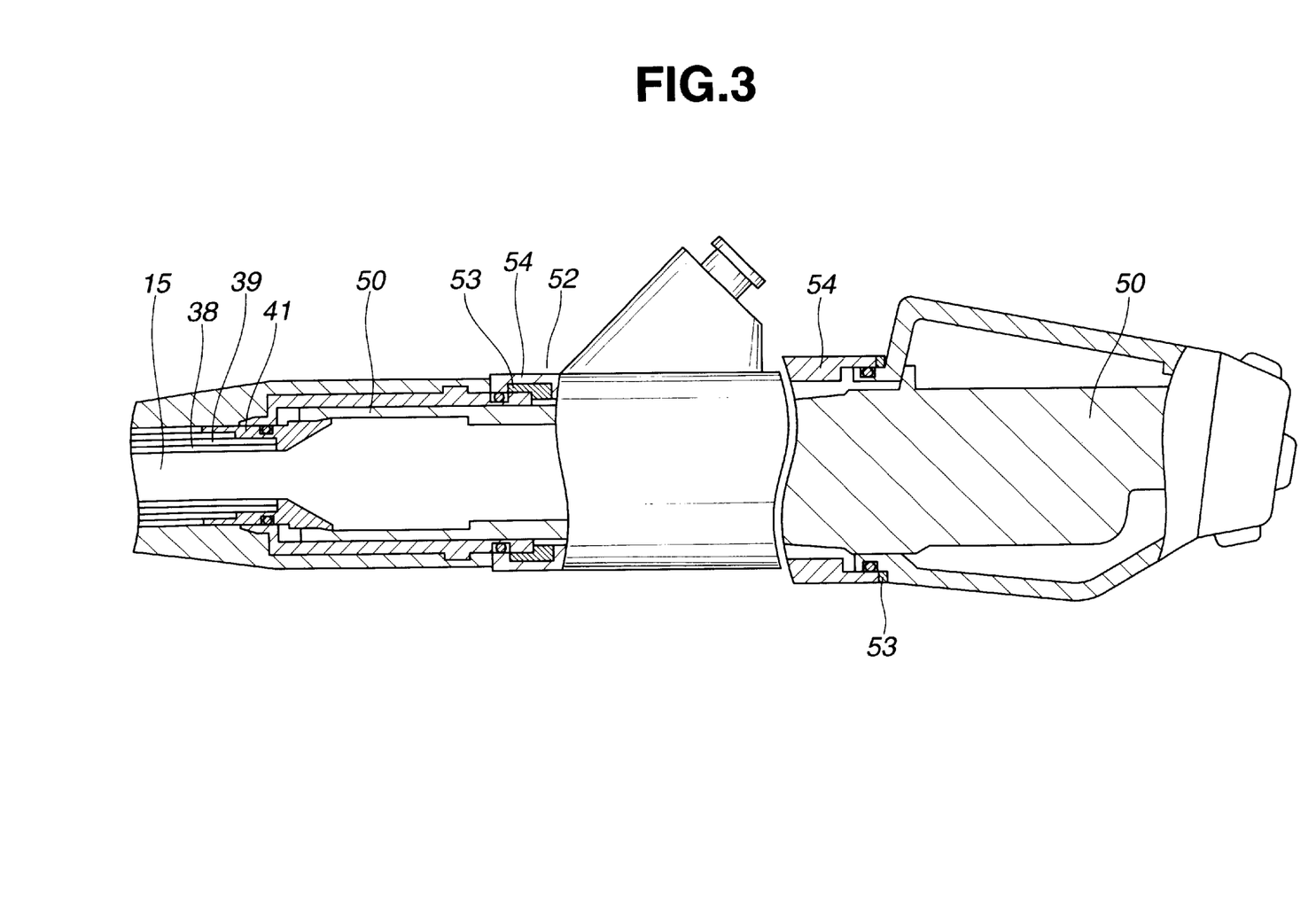
FIG. 3 is a sectional view showing the structures of a proximal part of the insertion member of the endoscope and a control section thereof.

Next, the proximal part of the insertion member 7 (flexible tube 15) and the control section 8 will be described referring to FIG. 3.

The proximal part of the insertion member 7 (flexible tube 15) has a connection base 41 made of a metal such as a stainless steel. The spiral tube 38 and braid 39 are fitted in the connection base 41. The outer surface of the braid 39 is brought into close contact with the inner wall of the connection base 41. The ends of the spiral tube 38 and braid 39 are contacted with the connection base 41.

The control section 8 has a chassis 50 that accommodates an angling mechanism which is not shown and which bends the bending section 16. The chassis 50 is made of a metal that exhibits excellent heat conductivity, such as, aluminum. The chassis 50 may be formed with a single metallic member or by joining a plurality of metallic members.

The distal end of the chassis 50 is engaged with the connection base 41 in which the proximal part of the flexible tube 15 is fitted. The proximal end of the chassis 50 is coupled to a connection base (not shown) of the universal cord 9. The connection base is made of a metal such as a stainless steel or aluminum. The universal cord 9 has the same structure as the flexible tube 15.

A control section casing 52 that seals the chassis 50 and the angling mechanism (not shown) in a watertight manner is mounted on the outer circumference of the chassis 50.

The control section casing 52 is formed with a plurality of members and includes a hand-held part casing 54 that is held by an operator. The hand-held part casing 54 is made of a resin that withstands high-temperature high-pressure steam sterilization, such as, polyphenylsulfone, polysulfone, polyethersulfone, polyether ether ketone, polyphenylene sulfide, polyetherimide, or a liquid crystal polymer.

The hand-held part casing 54 is structured not to come into contact with the chassis 50 and the angling mechanism (not shown). There is a space between the hand-held part casing 54 and the chassis 50 or angling mechanism.

Moreover, an adiabatic member 53 is interposed between the hand-held part casing 54 and each adjoining member. The adiabatic member 53 is made of a resin whose heat conductivity is lower than that of the hand-held part casing 54, an elastomer, or an expandable resin that contains minute air foam.

A feature of the endoscope provided by the present invention that will be described below is attained through appropriate selection of materials to be made into the members of the bending section 16 and the members of the control section 8. Otherwise, the feature is attained through selection of the method of joining members, setting of an area by which adjoining members are in contact with each other, setting an area by which the chassis 50 coupled to the flexible tube 15 and the hand-held part casing 54 are in contact with each other, or setting of the number of adiabatic members 53 to be interposed between the hand-held part casing 54 and the chassis 50.

Assuming that the ambient temperature ranges from, for example, about 36° C. to about 140° C., the feature provided by the present invention is such that: at the ambient temperature, a drop in the temperature of the outer surface of each of the insulating cover member 47, sheathing tube 45, sheathing layer 40, and adhesive 48 that constitute the outer surface of the insertion member 7 is larger than a drop in the temperature of the outer surface of the handheld part casing 54.

What is referred to as a drop in temperature signifies the value of temperature to which the temperature of a member is lowered in a certain period of time after the member of the predetermined temperature is cooled.

Moreover, the temperature 140° C. that is an upper limit of the temperature range is the highest temperature of the endoscope 2 heated during high-temperature high-pressure steam sterilization. The temperature 36° C. is substantially identical to the body temperature of a subject who has the insertion member 7 of the endoscope 2 inserted into his/her body cavity. At the temperature, the subject will not feel that something is wrong.

According to the present embodiment, a material whose heat conductivity is lower than the heat conductivities of the resin materials made into the insulating cover member 47, sheathing tube 45, sheathing layer 40, and adhesive 48 is adopted as the material of the hand-held part casing 54. For example, the insulating cover member 47 is made of polyethersulfone, and the sheathing tube 45 is made of a fluorocarbon rubber, the sheathing layer 40 is made of an amide elastomer, and the adhesive 48 is made of an epoxy resin. At this time, the hand-held part casing 54 is made of a resin whose heat conductivity is lower than the heat conductivities of-these materials. However, the heat conductivity of a resin base itself need not be the lowest. A glass fiber or any other resin material may be mixed in a resin base so that the mixture will exhibit low heat conductivity. The mixture is adopted as the material of the hand-held part casing 54.

Moreover, the metallic member whose heat conductivity is much higher than the heat conductivity of the above resin material is brought into contact with the inner surfaces of the insulating cover member 47, sheathing tube 45, and sheathing layer 40 that constitute the outer surface of the insertion member 7. Thus, the insulating cover member 47, sheathing tube 45, and sheathing layer 40 are linked with the metallic member. Furthermore, the insulating cover member 47, sheathing tube 45, and sheathing layer 40 are brought into contact with the chassis 50 that is a metallic member.

The hand-held part casing 54 is thermally insulated from the chassis 50 that is a metallic member to the greatest possible extent.

After the thus structured endoscope 2 is used to conduct endoscopic examination, the endoscope 2 is placed in a high-temperature high-pressure steam sterilizer (autoclave)

(not shown), and then autoclaved. An operation exerted at this time will be described below.

The endoscope 2 is heated up to approximately 140° C. during high-temperature high-pressure steam sterilization. The temperature at which the endoscope 2 is taken out of the sterilizer generally ranges from substantially 80° C. to 130° C. In order to reuse the endoscope for endoscopic examination, the endoscope may be naturally cooled down to predetermined temperature or may be forcibly cooled down thereto while being exposed to cool water or cool breeze.

According to the present invention, when the endoscope 2 is taken out of the sterilizer, the metallic members and chassis 50 are cooled. The metallic members and chassis 50 exhibit excellent heat conductivity and are in contact with the insulating cover member 47, sheathing tube 45, and sheathing layer 40, which constitute the outer surface of the insertion member 7. The heat dissipated by the insulating cover member 47, sheathing tube 45, and sheathing layer 40 that exhibit lower heat conductivities is conducted to the metallic members that are in contact therewith. This facilitates cooling of the insulating cover member 47, sheathing tube 45, and sheathing layer 40.

In contrast, the hand-held part casing 54 is not in contact with any metallic member that exhibits excellent heat conductivity, and thermally insulated owing to air surrounding the adiabatic members 53 and hand-held part casing 54. The hand-held part casing 54 is therefore hardly cooled.

Moreover, the material of the hand-held part casing 54 exhibits heat conductivity that is lower than the materials of the insulating cover member 47, sheathing tube 45, and sheathing layer 40. The hand-held part casing 54 is therefore harder to be cooled than the insulating cover member 47, sheathing tube 45, and sheathing layer 40 are.

Consequently, when certain time has elapsed since start of cooling, the temperature of the hand-held part casing 54 is higher than the temperature of any other part of the outer surface of the insulating member 7.

When the hand-held part casing 54 is held in order to check the temperature thereof, if the temperature is recognized to be too high to permit use of the endoscope for examination, the endoscope 2 is further cooled. If the temperature of the hand-held part casing 54 is recognized to be low enough to permit use of the endoscope, the temperature of the insertion member 7 is undoubtedly lower than that of the hand-held part casing 54. Consequently, by checking the temperature of the hand-held part casing 54, it can be recognized whether the temperature of the insertion member 7 is low enough to permit use of the endoscope.

Consequently, whether the temperature of the insertion member 7 is low enough to permit use of the endoscope for examination can be reliably and easily known without the necessity of touching the insertion member 7.

Alternatively, a drop in the temperature of the hand-held part casing 54 occurring in certain time may be substantially equal to the smallest drop among the drops in the temperatures of the insulating cover member 47, sheathing tube 45, sheathing layer 40, and adhesive 48 (that is, the temperature of a member hardly cooled). Nevertheless, the same operation and advantage as the described ones can be obtained.

Generally, an operator holds the insertion member 7, inserts it into a body cavity, and then starts an examination. At this time, the operator tends to hold the flexible tube 15 and may insert the flexible tube 15 without touching the bending section 16 and distal part 17 at all.

Therefore, before an examination is started, when the flexible tube 15 is held, the temperature thereof may be checked. Thus, it may be known whether the temperatures of the bending section 16 of the insertion member 7 and the distal part 17 thereof are low enough to permit use of the endoscope for examination.

In this case, when the ambient temperature falls within a predetermined range of temperatures, that is, ranges, for example, from about 36° C. to about 140° C., the drops in the temperatures of the insulating cover member 47 of the distal part 17, the sheathing tube 45, and the sheathing layer 40 of the flexible tube 15 are determined so that the drop in the temperatures of the insulating cover member 47 and sheathing tube 45 will be the same as the drop in the temperature of the outer surface of the sheathing layer 40. Otherwise, the drop in the temperature of the sheathing layer 40 is made larger than the drop in the temperatures of the insulating cover member 47 and sheathing tube 45.

In this case, the insulating cover member 47 and sheathing tube 45 may be made of a material that exhibits higher heat conductivity than the material of the sheathing. layer 40. Areas by which the insulating cover member 47 and sheathing tube 45 are in contact with the distal body 46, braid 44, and articulation members 43 that are metallic members may be increased so that heat can be more readily conducted to the metallic members which exhibit excellent heat conductivity. Moreover, an adiabatic layer may be formed between the sheathing layer 40 and the spiral tube 38 or braid 39 that is a metallic member in contact with the sheathing layer 40 in order to prevent ready conduction of heat. The adiabatic layer may be formed with an adhesive whose heat conductivity is low, or a minute air layer may be formed in an adhesive layer. Moreover, the braid 39 may be made by mixing a Kevler fiber, of which heat conductivity is low, in metallic wires instead of plaiting metallic wires alone. Thus, an area occupied by a metal on a contact surface may be reduced.

After the thus structured endoscope 2 is autoclaved using an autoclave that (not shown), the endoscope 2 is cooled at predetermined ambient temperature. The outer surface of the bending section 16 of the insertion member 7 of the endoscope 2, and the outer surface of the distal part 17 thereof, that is, the insulating cover member 47 and sheathing tube 45 are more likely to be cooled than the outer surface of the flexible tube 15 that is the sheathing layer 40. When certain time has elapsed since the start of cooling, the temperatures of the insulating cover member 47 and sheathing tube 45 become equal to or lower than the temperature of the sheathing layer 40.

Therefore, before an endoscopic examination is started, when the flexible tube 15 is held, the temperature of the flexible tube 15 is checked. If the temperature is too high to permit use of the endoscope for examination, cooling is carried out. If the temperature is low enough to permit use of the endoscope for examination, the temperatures of the outer surfaces of the bending section 16 and distal part 17 are undoubtedly equal to or lower than the temperature of the outer surface of the flexible tube 15. The endoscope is therefore usable.

Consequently, whether the temperature is low enough to permit use of the endoscope. for examination can be reliably and easily known without the necessity of touching the bending section 16 and distal part 17.

According to the present invention, setting of the heat conductivities of materials and presence or absence of an adiabatic member need not be performed as they are in the aforesaid embodiment. Various components should be combined so that the drops in the temperatures of the outer surfaces thereof occurring in certain time will have predetermined relationships.

According to the present invention, it is apparent that a wide range of different embodiments can be formed based on the invention without a departure from the spirit and scope of the invention. Moreover, the present invention is limited to the appended claims but not restricted to any specific embodiments.

What is claimed is:

1. An endoscope capable of undergoing at least one of cleaning, disinfection, and sterilization at high temperature, comprising:

an elongated insertion member; and a control section joined to the proximal end of said insertion member, wherein a drop in the temperature of at least part of the outer surface of said insertion member occurring when said endoscope is cooled to predetermined temperature after processed at high temperature is substantially equal to or larger than a drop in the temperature of at least part of the outer surface of any member other than said part of the outer surface of said insertion member.

2. An endoscope according to claim 1, wherein a member forming at least part of the outer surface of any member other than said part of the outer surface of said insertion member is thermally insulated from another member adjoining the member.

3. An endoscope according to claim 1, wherein a drop in the temperature of at least part of the outer surface of said insertion member is substantially equal to or larger than a drop in the temperature of at least part of the outer surface of said control section.

4. An endoscope according to claim 3, wherein said at least part of the outer surface of said control section is part of the outer surface of a hand-held part of said control section.

5. An endoscope according to claim 1, wherein said at least part of the outer surface of said insertion member is at least part of the outer surface of a flexible tube that includes a soft sheathing of said insertion member.

6. An endoscope according to claim 5, wherein a drop in the temperature of at least part of the outer surface of said flexible tube is substantially equal to or larger than a drop in the temperature of at least part of the outer surface of said control section.

7. An endoscope according to claim 6, wherein said at least part of the outer surface of said control section is at least part of the outer surface of a hand-held part of said control section.

8. An endoscope according to claim 1, wherein said at least part of the outer surface of said insertion member is at least part of the outer surface of a member that is distal to a bending section of said insertion member.

9. An endoscope according to claim 8, wherein a drop in the temperature of at least part of the outer surface of the member that is distal to the bending section is substantially equal to or larger than a drop in the temperature of at least part of the outer surface of said control section.

10. An endoscope according to claim 9, wherein said at least part of the outer surface of said control section is at least part of the outer surface of a hand-held part of said control section.

11. An endoscope according to claim 8, wherein a drop in the temperature of at least part of the outer surface of a member that is distal to a bending section of said insertion member is substantially equal to or larger than a drop in the temperature of at least part of the outer surface of a flexible tube proximal to the bending section.

12. An endoscope according to claim 1, wherein a member forming at least part of the outer surface of said insertion member is made of a material whose heat conductivity is higher than the heat conductivity of a member forming at least part of the outer surface of any member other than said part of the outer surface of said insertion member.

13. An endoscope according to claim 12, wherein a :member forming at least part of the outer surface of any member other than said part of the outer surface of said insertion member is thermally insulated from another member adjoining the member.

14. An endoscope according to claim 1, wherein said endoscope is sterilized with high-temperature high-pressure steam and exposed to the temperature ranging from substantially 36° C. to 140° C.

15. An endoscope capable of undergoing at least one of cleaning, disinfection, and sterilization at high temperature, comprising:

an elongated insertion member; and a control section joined to the proximal end of said insertion member, wherein a drop in the temperature of at least part of the outer surface of said insertion member occurring when said endoscope is cooled to predetermined temperature after being processed at high temperature is substantially equal to or larger than a drop in the temperature of at least part of the outer surface of any member other than said insertion member.

16. An endoscope according to claim 15, wherein a drop in the temperature of at least part of the outer surface of said insertion member is substantially equal to or larger than a drop in the temperature of at least part of the outer surface of said control section.

17. An endoscope according to claim 16, wherein said at least part of the outer surface of said control section is at least part of the otter surface of a hand-held part of said control section.

18. An endoscope according to claim 15, wherein said at least part of the outer surface of said insertion member is at least part of the outer surface of a flexible tube that includes a soft sheathing of said insertion member.

19. An endoscope according to claim 18, wherein a drop in the temperature of at least part of the outer surface of said flexible tube is substantially equal to or larger than a drop in the temperature of at least part of the outer surface of said control section.

20. An endoscope according to claim 19, wherein said at least part of the outer surface of said control section is at least part of the outer surface of a hand-held part of said control section.

21. An endoscope according to claim 15, wherein said at least part of the outer surface of said insertion member is at least part of the outer surface of a member that is distal to a bending section of said insertion member.

22. An endoscope according to claim 21, wherein a drop in the temperature of at least part of the outer surface of a member that is distal to said bending section is substantially equal to or larger than a drop in the temperature of at least part of the outer surface of said control section.

23. An endoscope according to claim 22, wherein said at least part of the outer surface of said control section is at least part of the outer surface of a hand-held part of said control section.

24. An endoscope according to claim 21, wherein a drop in the temperature of at least part of the outer surface of a member that is distal to a bending section of said insertion member is substantially equal to or larger than a drop in the temperature of at least part of the outer surface of a flexible tube that is proximal to the bending section.

25. An endoscope according to claim 15, wherein a member forming at least part of the outer surface of said insertion member is made of a material whose heat conductivity is higher than the heat conductivity of a member forming at least part of the outer surface of any member other than said insertion member.

26. An endoscope according to claim 25, wherein a member forming at least part of the outer surface of any member other than said insertion member is thermally insulated from another member adjoining the member.

27. An endoscope according to claim 15, wherein said endoscope is sterilized with high-temperature high-pressure steam and exposed to temperature ranging from substantially 36° C. to 140° C.

* * * * *